United States Patent [19]
Montana

[11] Patent Number: 6,124,288
[45] Date of Patent: Sep. 26, 2000

[54] XANTHINES AND THEIR THERAPEUTIC USE

[75] Inventor: John Gary Montana, Cambridge, United Kingdom

[73] Assignee: Darwin Discovery, Ltd., United Kingdom

[*] Notice: This patent issued on a continued prosecution application filed under 37 CFR 1.53(d), and is subject to the twenty year patent term provisions of 35 U.S.C. 154(a)(2).
This patent issued on a continued prosecution application filed under 37 CFR 1.53(d), and is subject to the twenty year patent term provisions of 35 U.S.C. 154(a)(2).
This patent is subject to a terminal disclaimer.

[21] Appl. No.: 09/169,616

[22] Filed: Oct. 9, 1998

Related U.S. Application Data

[63] Continuation of application No. 08/650,231, May 20, 1996, Pat. No. 5,821,366.

[30] Foreign Application Priority Data

| May 19, 1995 | [GB] | United Kingdom | 9510185 |
| Nov. 20, 1995 | [GB] | United Kingdom | 9523680 |

[51] Int. Cl.⁷ .................. A61K 31/522; A61K 31/5377; C07D 473/04; C07D 473/06
[52] U.S. Cl. ............ 514/234.2; 514/263; 514/265; 544/118; 544/267; 544/268; 544/269; 544/270; 544/271; 544/272; 544/273
[58] Field of Search .............. 514/234.2; 544/267, 544/268, 272

[56] References Cited

U.S. PATENT DOCUMENTS

| 5,223,504 | 6/1993 | Noverola | 544/267 |
| 5,821,366 | 10/1998 | Montana | 544/267 |

FOREIGN PATENT DOCUMENTS

| 0369744 | 5/1990 | European Pat. Off. . |
| 0389282 | 9/1990 | European Pat. Off. . |
| 0541120 | 5/1993 | European Pat. Off. . |
| 541120 | 5/1993 | European Pat. Off. . |
| 8601724 | 3/1986 | WIPO . |
| 9205175 | 4/1992 | WIPO . |
| 9205176 | 4/1992 | WIPO . |
| 9211260 | 7/1992 | WIPO . |
| 94-00452 | 1/1994 | WIPO . |
| 9400452 | 1/1994 | WIPO . |

OTHER PUBLICATIONS

Jacob, J. Autoimmunity 5, Supp. A, 133, 1992.
Jacob, C.O. (1992) Studies on the Role of Tumor Necrosis Factor in Murine and Human Autoimmunity. Journal of Autoimmunity 5(Supl. A): 133–143.
Ram, V.J., H.K. Pandey, A.J. Vlietinck (1982) Purine Analogues As Potential Chemotherapeutic Agents. III. J. Heterocyclic Chem. 19: 153–155.
Merlos, M. et al. (1990) Structure–activity relationships in a series of xanthine derivatives with antibronchoconstrictory and bronchodilatory activities. Eur. J. Med. Chem. 25:653–658.

*Primary Examiner*—Mark L. Berch
*Attorney, Agent, or Firm*—Saliwanchik, Lloyd & Saliwanchik

[57] ABSTRACT

The subject invention concerns a compound of the formula (i):

in which Q represents heteroaryl or heterocyclo optionally substituted with one or more substituents selected from the group consisting of $C_{1-6}$ alkyl (optionally substituted with one or more halogens), $C_{1-6}$ alkyl—S(O)n— (where n is 0, 1 or 2), —$CO_2H$ (or $C_{1-6}$ alkyl esters thereof or $C_{1-6}$ alkyl amides thereof), halogen, $C_{1-6}$ alkoxy, CN, $NO_2$ and $NR_7R_8$;

$R_1$–$R_5$, which may be the same or different, each represent $C_{1-6}$ alkyl (optionally substituted with one or more halogens), $C_{1-6}$ alkyl—S(O)n— (where n is 0, 1 or 2), —$CO_2H$ (or $C_{1-16}$ alkyl esters thereof or $C_{1-6}$ alkyl amides thereof), halogen, $C_{1-6}$ alkoxy, CN, $NO_2$, $NR_7R_8$ or H (provided $R_1$–$R_6$ are not all H simultaneously);

$R_6$ represents H, $C_{1-6}$ alkyl, —$CO_2H$ (or $C_{1-6}$ alkyl esters thereof or $C_{1-6}$ alkyl amides thereof), —CN, $C_{1-6}$ alkyl optionally substituted by —$CO_2H$ (or $C_{1-6}$ alkyl esters thereof or $C_{1-6}$ alkyl amides thereof), $C_{1-6}$ alkoxy or —CN; and $R^7$ and $R_8$, which may be the same or different, each represent H, $C_{1-6}$ alkyl, $C_{1-6}$ Alkylcarbonyl, $C_{1-6}$ alkoxycarbonyl, arylsulphonyl, heteroarylsulphonyl, heterocyclosulphonyl, arylcarbonyl, heteroarylcarbonyl, heterocyclocarbonyl or $C_{1-6}$ alkylsulphonyl, or $R_7$, $R_8$ and the nitrogen to which they are attached form a 5 or 6 membered heterocyclic ring;

and pharmaceutically-acceptable salts thereof.

9 Claims, No Drawings

XANTHINES AND THEIR THERAPEUTIC USE

This is a continuation of 08/650231 filed May 20, 1996 now U.S. Pat. No. 4,821,366.

FIELD OF THE INVENTION

The present invention relates to novel xanthine compounds and pharmaceutically acceptable salts thereof, processes for their production and their formulation and use as pharmaceuticals.

DESCRIPTION OF THE PRIOR ART

Xanthine compounds such as theophylline (The Merck Index, 11th edition, 9212), pentoxifylline (The Merck Index, 11th edition 7092). and propentofylline (The Merck Index, 11th edition, 7822) have been widely used clinically for the treatment of respiratory tract disease or brain dysfunction. The chief clinical disadvantages of xanthine compounds are severe adverse reactions frequently induced by the administration of these compounds. Examples of the adverse reactions are, for example, cardio-excitatory activity such as, for example, cardiopalmus or tachycardia; central activity such as, for example, convulsion or headache; and gastrointestinal activity such as for example, nausea or emesis. Therefore, xanthine compounds without these adverse reactions would provide significant clinical benefit.

Related xanthine derivatives have been disclosed as pesticidal and pestistatic agents (U.S. Pat. No. 4,883,801). In addition, related xanthine derivatives have been disclosed as intermediates but no pharmacological activity is disclosed for these compounds (European Patent Application No. 0 369 744, International Patent Application WO 92/05176, European Patent Application No. 0 389 282 and International Patent application WO 94/00452).

Phosphodiesterases regulate cyclic AMP concentrations. Phosphodiesterase IV has been demonstrated to be a principal regulator of cyclic AMP in respiratory smooth muscle and inflammatory cells. [See Torphy and Creslinski, *Molecular Pharmacology* 37, 206, (1990); Dent et al *British Journal of Pharmacology*, 90 163p (1990)]. Inhibitors of phosphodiesterase IV have been implicated as being bronchodilators and asthma-prophylactic agents and as agents for inhibiting eosinophil accumulation and the function of eosinophils [see for example Giembycz and Dent, *Clinical and Experimental Allergy* 22 337 (1992)] and for treating other diseases and conditions characterised by, or having an etiology including, morbid eosinophil accumulation. Inhibitors of phosphodiesterase IV are also implicated in treating inflammatory diseases, proliferative skin disease and conditions associated with cerebral metabolic inhibition.

Excessive or unregulated production of Tumour Necrosis Factor (TNF) has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as Kupffer and glial cells, have also been implicated in maintenance of the HIV infection. These cells, like T cells, are targets for viral replication and the level of viral replication is dependent upon the activation state of the cells. [See Rosenberg et al, The Immunopathogenesis of HIV Infection, Advances in Immunology, Vol. 57, (1989)]. Monokines, such as TNF, have been shown to activate HIV replication in monocytes and/or macrophages [See Poli et al, Proc. Natl. Acad. Sci., 87:782–784, (1990)], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted above.

TNF is also associated with yeast and fungal infections. Specifically *Candida albicans* has been shown to induce TNF production in vitro in human monocytes and natural killer cells [See Riipi et al., Infection and Immunity, 58(9):2750–54, (1990); and Jafari et al., Journal of Infectious Diseases, 164:389–95, (1991). See also Wasan et al., Antimicrobial Agents and Chemotherapy, 35, (10):2046–48, (1991); and Luke et al., Journal of Infectious Diseases, 162:211–214, (1990)].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

It has been found that novel compounds have ability to treat disease states, for example disease states associated with proteins that mediate cellular activity, for example by inhibiting tumour necrosis factor and/or by inhibiting phosphodiesterase IV. According to the invention, the novel compounds are of formula (i):

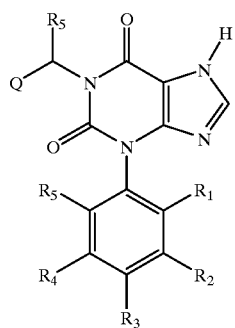

(i)

in which Q represents aryl, heteroaryl, cycloalkyl or heterocyclo optionally substituted with one or more substituents chosen from amongst $C_{1-6}$ alkyl (optionally substituted with one or more halogens), $C_{1-6}$ alkyl—S(O)n—, —$CO_2H$ (or $C_{1-6}$ alkyl esters thereof or $C_{1-6}$ alkyl amides thereof), halogen, $C_{1-6}$ alkoxy, CN, $NO_2$ or $NR_7R_8$;

$R_1$–$R_5$, which may be the same or different, each represent $C_{1-6}$ alkyl (optionally substituted with one or more halogens), $C_{1-6}$ alkyl—S(O)n—, —$CO_2H$ (or $C_{1-6}$ alkyl esters thereof or $C_{1-6}$ alkyl amides thereof), halogen, $C_{1-6}$ alkoxy, CN, $NO_2$, $NR_7R_8$ or H (provided $R_1$–$R_6$ are not all H simultaneously);

$R_6$ represents H, $C_{1-6}$ alkyl, —$CO_2H$ (or $C_{1-6}$ alkyl esters thereof or $C_{1-6}$ alkyl amides thereof), —CN, $C_{1-6}$ alkyl optionally substituted by —$CO_2H$ (or $C_{1-6}$ alkyl esters thereof or $C_{1-6}$ alkyl amides thereof), $C_{1-6}$ alkoxy or —CN;

$R_7$ and $R_8$, which may be the same or different, and each represent H, $C_{1-6}$ alkyl, $C_{1-6}$ alkylcarbonyl, $C_{1-6}$ alkoxycarbonyl, arylsulphonyl, heteroarylsulphonyl, heterocyclosulphonyl, arylcarbonyl, heteroarylcarbonyl, heterocyclocarbonyl or $C_{1-6}$ alkylsulphonyl, or $R_7$, $R_8$ and the nitrogen to which they are attached form a 5 or 6 membered heterocyclic ring (such as morpholine or piperidine); and n represents 0–2;

and pharmaceutically acceptable salts.

DESCRIPTION OF THE INVENTION

Preferred compounds of the invention include those in which, independently or in any combination:

Q is aryl or heteroaryl (either may be optionally substituted with halogen, $C_{1-6}$ alkyl, $CF_3$, $NR_7R_8$, $C_{1-6}$ alkyl—S(O)n—, $C_{1-6}$ alkoxy, —$CO_2H$ (or $C_{1-6}$ alkyl esters thereof or $C_{1-6}$ alkyl amides thereof));

$R_1$–$R_5$, which may be the same or different, are independently $CF_3$, $C_{1-6}$ alkyl, $C_{1-6}$ alkyl—S(O)n—, —$CO_2H$ (or $C_{1-6}$ alkyl esters thereof or $C_{1-6}$ alkyl amides thereof), halogen, $C_{1-6}$ alkoxy, $NO_2$, $NR_7R_8$ or H (provided $R_1$–$R_5$ are not all H simultaneously);

$R_6$ is H;

$R_7$ and $R_8$, which may be the same or different, are H, $C_{1-6}$ alkyl, $C_{1-6}$ alkoxycarbonyl, $C_{1-6}$ alkylsulphonyl or $C_{1-6}$ alkylcarbonyl; or $R_7$, $R_8$ and the nitrogen to which they are attached form a 5 or 6 membered heterocyclic ring (such as morpholine or piperidine); and n is 0,1 or 2.

Suitable pharmaceutically acceptable salts are pharmaceutically acceptable base salts and pharmaceutically acceptable acid addition salts. Certain of the compounds of formula (i) which contain an acidic group form base salts.

Suitable pharmaceutically acceptable base salts include metal salts, such as alkali metal salts for example sodium salts, or organic amine salts such as that provided with ethylenediamine.

Certain of the compounds of formula (i) which contain an amino group form acid addition salts. Suitable acid addition salts include pharmaceutically acceptable inorganic salts such as the sulphate, nitrate, phosphate, borate, hydrochloride and hydrobromide and pharmaceutically acceptable organic acid addition salts such as acetate, tartrate, maleate, citrate, succinate, benzoate, ascorbate, methane-sulphate, α-ketoglutarate, α-glycerophosphate and glucose-1-phosphate. The pharmaceutically acceptable salts of the compounds of formula (i) are prepared using conventional procedures.

It will be appreciated by those skilled in the art that xanthines of formula (i) can exist in more than one tautomeric form. This invention extends to all tautomeric forms.

It will be appreciated that the compounds according to the invention can contain one or more asymmetrically substituted carbon and/or sulphur atoms. The presence of one or more of these asymmetric centers in a compound of formula (i) can give rise to stereoisomers, and in each case the invention is to be understood to extend to all such stereoisomers, including enantiomers, and diastereoisomers and mixtures including racemic mixtures thereof.

When used herein the term alkyl whether used alone or when used as part of another group includes straight and branched chain alkyl groups containing up to 6 atoms. Cycloalkyl includes a non-aromatic cyclic or multicyclic ring system of about 3 to about 10 carbon atoms. Alkoxy means an alkyl—O— group in which the alkyl group is as previously described. Alkyl amide includes both monoalkyl and dialkyl amides, in which the alkyl groups previously defined) may be the same or different. Alkylcarbonyl means an alkyl—CO— group in which the alkyl group is as previously described. Aryl indicates a monocyclic or multicyclic carbocyclic radical containing about 6 to 10 carbon atoms. Heteroaryl means about a 5 to about a 10 membered aromatic monocyclic or multicyclic hydrocarbon ring system in which one or more of the atoms in the ring system is an element other than carbon, chosen from amongst nitrogen, oxygen or sulphur. Heterocyclo means about a 5 to about a 10 membered saturated or partially saturated monocyclic or multicyclic hydrocarbon ring system in which one or more of the atoms in the ring system is an element other than carbon, chosen from amongst nitrogen, oxygen or sulphur. Arylcarbonyl means an aryl—CO— group. Heteroarylcarbonyl means a heteroaryl—CO— group. Heterocyclocarbonyl means a heterocyclo—CO— group. Arylsulphonyl means an aryl—$SO_2$— group. Heteroarylsulphonyl means a heteroaryl—$SO_2$— group. Heterocyclosulphonyl means a heterocyclo—$SO_2$— group. Alkylsulphonyl means an alkyl—$SO_2$— group. Halogen means fluorine, chlorine, bromine or iodine.

"TNF mediated disease or disease states" means any and all disease states in which TNF plays a role, either by production of TNF itself, or by TNF causing another cytokine to be released, such as but not limited to IL-1 or IL-6. A disease state in which IL-1, for instance, is a major component, and whose production or action is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise.

This invention relates to a method for mediating or inhibiting the enzymatic activity or catalytic activity of PDE IV in a mammal in need thereof and for inhibiting the production of TNF in a mammal in need thereof, which comprises administering to said mammal an effective amount of a compound of Formula (i) or a pharmaceutically acceptable salt thereof.

PDE IV inhibitors are useful in the treatment of a variety of allergic and inflammatory diseases, including: asthma, chronic bronchitis, atopic dermatitis, atopic eczema, urticaria, allergic rhinitis, allergic conjunctivitis, vernal conjunctivitis, inflammation of the eye, allergic responses in the eye, eosinophilic granuloma, psoriasis, Bechet's disease, erythematosis, anaphylactoid purpura nephritis, joint inflammation, arthritis, rheumatoid arthritis and other arthritic conditions such as rheumatoid spondylitis and osteoarthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus and conditions associated with cerebral metabolic inhibition, such as cerebral senility, senile dementia (Alzheimer's disease), memory impairment associated with Parkinson's disease, depression and multi-infarct dementia. PDE IV inhibitors are also useful in conditions ameliorated by neuroprotectant activity, such as cardiac arrest, stroke and intermittent claudication. Additionally, PDE IV inhibitors could have utility as gastroprotectants. A special embodiment of the therapeutic methods of the present invention is the treatment of asthma.

The viruses contemplated for treatment herein are those that produce TNF as a result of infection, or those which are sensitive to inhibition, such as by decreased replication, directly or indirectly, by the TNF inhibitors of Formula (i). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (i) or a pharmaceutically acceptable salt thereof.

The compounds of this invention may be also be used in association with the veterinary treatment of animals, other than humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anaemia virus, caprine arthritis virus, visna virus, maedi virus and other lentiviruses.

The compounds of this invention are also useful in treating parasite, yeast and fungal infections, where such yeast and fungi are sensitive to upregulation by TNF or will elicit TNF production in vivo. A preferred disease state for treatment is fungal meningitis.

The compounds of formula (i) are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

The invention further provides a process for the preparation of a compound of formula (i), in which $R_1$–$R_6$ are as defined above. It will be appreciated that functional groups such as amino, hydroxyl or carboxyl groups present in the various compounds described below, and which it is desired to retain, may need to be in protected forms before any reaction is initiated. In such instances, removal of the protecting group may be the final step in a particular reaction. Suitable protecting groups for such functionality will be apparent to those skilled in the art. For specific details, see Protective Groups in Organic Synthesis, Wiley Interscience, T W Greene.

Thus the process required for preparing compounds of formula (i) in which $R_6$ is —$CO_2H$ comprises of deprotecting (for example by hydrolysis) a compound of formula (i) in which $R_6$ is —$CO_2R$ wherein R represents a suitable protecting group (eg, methyl).

It will be appreciated that where a particular stereoisomer of formula (i) is required, this may be obtained by conventional resolution techniques such as high performance liquid chromatography or the synthetic processes herein described may by performed using the appropriate homochiral starting material.

A process for the preparation of a compound of formula (i) comprises a dehydrating cyclisation of a compound of formula (ii):

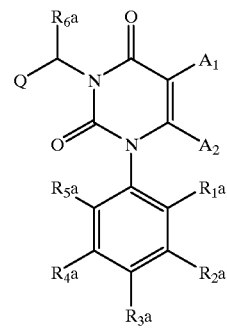

(ii)

wherein $R_{1a}$ represents $R_1$, as defined in relation to formula (i), or a group convertable to $R_{1a}$ and $R_{2a}$–$R_{6a}$ similarly represent $R_2$–$R_6$ or groups convertable to $R_2$–$R_6$, respectively; $A_1$ represents —NO or —NHCHO and $A_2$ represents —$NHCH_3$ or —$NH_2$, providing that when $A_1$ is —NO then $A_2$ is $NHCH_3$ and when $A_1$ is NHCHO then $A_2$ is $NH_2$; and thereafter, if required, converting any group $R_{1a}$ to $R_1$ and/or $R_{2a}$ to $R_2$ and/or $R_{3a}$ to $R_3$ and/or $R_{4a}$ to $R_4$ and/or $R_{5a}$ to $R_5$ and/or $R_{6a}$ to $R_6$. The dehydrating cyclisation of a compound of formula (ii) may be carried out under any suitable conditions known to those skilled in the art. Favourably the conditions chosen are those wherein the water formed is removed from the reaction mixture, thus the reaction is generally carried out at an elevated temperature in the range 100° C. to 200° C., such as in the range 180° C. to 190° C.

In one aspect of the process, especially when $A_1$ is —NO and $A_2$ is —$NHCH_3$, the reaction is carried out in a solvent immiscible with water, such as toluene, at the reflux temperature of the solvent, the water being removed using a water separator.

A compound of formula (ii) wherein $A_1$ represents —NHCHO and $A_2$ represents —$NH_2$ may be suitably prepared from a 6-aminouracil of formula (iii) according to the following reaction scheme:

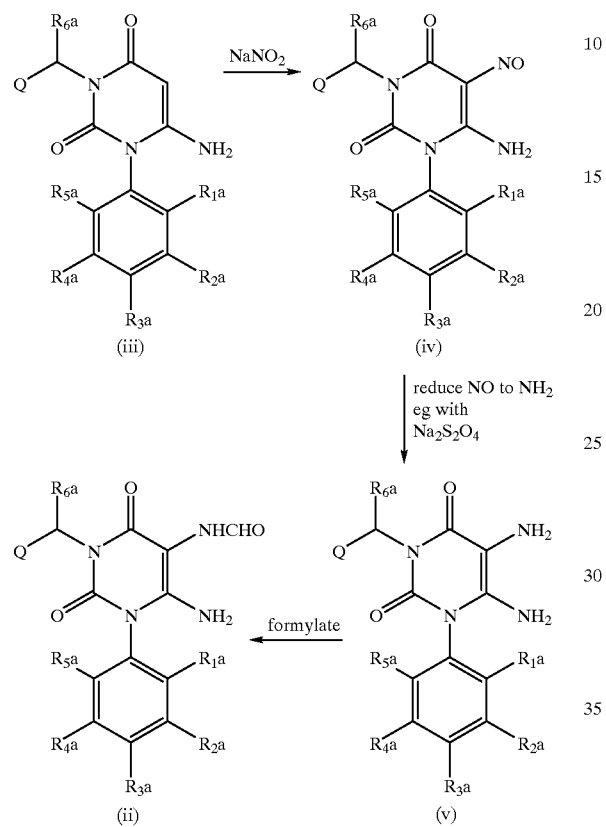

(iii) (iv) (ii) (v)

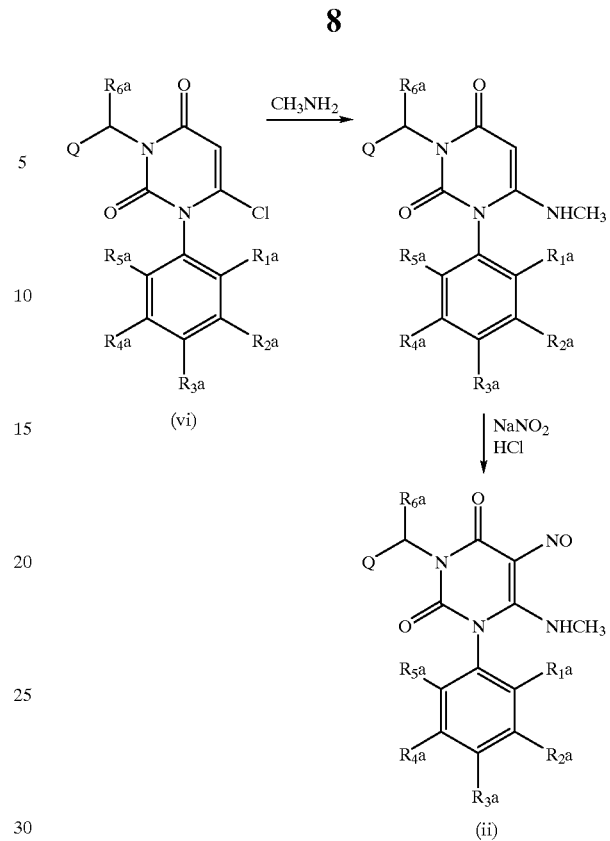

(vi) (ii)

wherein $R_{1a}$–$R_{6a}$ are as defined in relation to formula (ii).

Suitably, the reaction conditions used in the above reaction scheme are appropriate conventional conditions known to those skilled in the art. In a preferred aspect of the process, the conversion of the 6-aminouracil (iii), via (iv) and (v), to the corresponding compound of formula (ii) and the cyclisation of the compound of formula (ii) to the compound of formula (i) are all carried out in situ, suitably by using an analogous procedure to that of H. Bredereck and A. Edenhofer, *Chem. Berichte* 88 1306–1312 (1955).

The 6-aminouracils of formula (iii) may themselves be prepared by the method of V. Papesch and E. F. Schroder, *J. Org. Chem.* 16 1879–90 (1951), or Yozo Ohtsuka, *Bull. Chem. Soc. Jap.* 46(2) 506–9 (1973) or modifications of these methods.

A compound of formula (ii) wherein $A_1$ represents —NO and $A_2$ represents —$NHCH_3$ may conveniently be prepared from a 6-chlorouracil of formula (vi) according to the following reaction scheme:

wherein $R_{1a}$–$R_{6a}$ are as defined in relation to formula (ii).

Suitably, the reaction conditions used in the above scheme are the appropriate conventional conditions, for example those used in the method of H. Goldner, G. Dietz and E. Carstens, *Liebigs Annalen der Chemie* 691 142–158 (1965). The 6-chlorouracil of formula (vi) may also be prepared according to the procedure of Dietz et al.

Alternatively, compounds of formula (i) may be prepared according to the following reaction scheme:

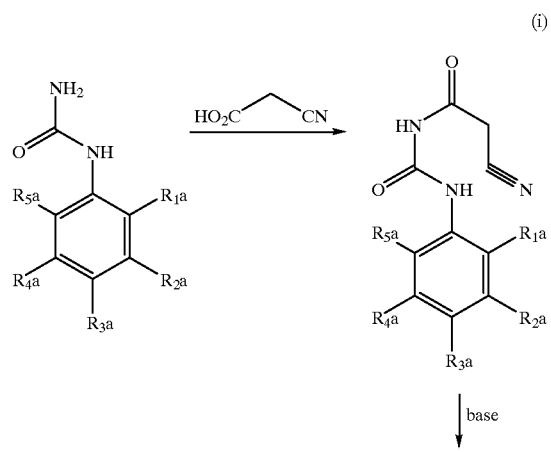

-continued

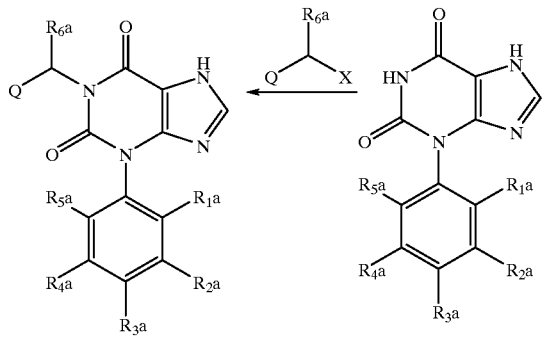

wherein $R_{1a}$–$R_{6a}$ are as defined in relation to formula (ii) and X is an appropriate leaving group such as bromo. Suitably the reaction conditions used in the above reaction scheme are standard conditions known to those skilled in the art.

Another method for the preparation of some compounds of formula (i) (based on a method described by C. E. Muller, D. Shi, M. Manning and J. W. Daly in *J. Med. Chem.* 36 3341(1993)) is shown in the following reaction scheme:

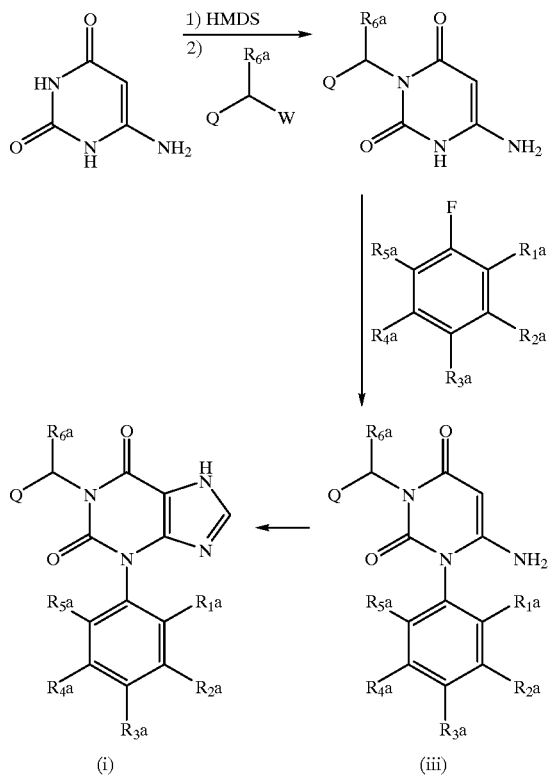

wherein $R_{1a}$–$R_{6a}$ are as defined in relation to formula (ii) and W represents a leaving group such as bromo. It will be appreciated by those skilled in the art that this method will not be applicable if any of $R_{1a}$–$R_{5a}$a represents fluoro.

Compounds of formula (i) may also be prepared by interconversion of other compounds of formula (i). Thus, for example, a compound of formula (i) in which $R_1$ is $NH_2$ may be prepared by reduction of a compound of formula (i) in which $R_1$ is $-NO_2$.

A compound of formula (i) or where appropriate a pharmaceutically acceptable salt thereof and/or a pharmaceutically acceptable solvate thereof, may be administered per se or, preferably, as a pharmaceutical composition also comprising a pharmaceutically acceptable carrier.

Accordingly, the present invention provides a pharmaceutical composition comprising a compound of formula (i) or where appropriate a pharmaceutically acceptable salt thereof and/or a pharmaceutically acceptable solvate thereof, and a pharmaceutically acceptable carrier.

The active compound may be formulated for administration by any suitable route, the preferred route depending upon the disorder for which treatment is required, and is preferably in unit dosage form or in a form that a human patient may administer to himself in a single dosage. Advantageously, the composition is suitable for oral, rectal, topical, parenteral administration or through the respiratory tract. Preparations may be designed to give slow release of the active ingredient.

The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc, the compounds of the invention are effective in the treatment of humans.

The compositions of the invention may be in the form of tablets, capsules, sachets, vials, powders, granules, lozenges, suppositories, reconstitutable powders, or liquid preparations such as oral or sterile parenteral solutions or suspensions. Topical formulations are also envisaged where appropriate.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers for example microcrystalline cellulose, lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers.

Such operations are of course conventional in the art. The tablets may be coated according to methods well known in normal pharmaceutical practice, in particular with an enteric coating.

Oral liquid preparations may be in the form of, for example, emulsions, syrups or elixirs, or may be presented as a dry product for reconstitution with water or other suitable vehicle before use. Such liquid preparations may contain conventional additives such as suspending agents, for example sorbitol, syrup, methylcellulose, gelatin, hydroxyeteylcellulose, carboxymethylcellulose, aluminium stearate gel, hydrogenated edible fats; emulsifying agents, for example lecithin, sorbitan monooleate, or a acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

Compositions may also suitably be presented for administration to the respiratory tract as a snuff or an aerosol or solution for a nebuliser, or as a microfine powder for insufflation, alone or in combination with an inert carrier such as lactose. In such a case the particles of active compound suitably have diameters of less than 50 microns, such as from 0.1 to 50 microns, preferably less than 10 microns, for example from 1 to 10 microns, 1 to 5 microns or from 2 to 5 microns. Where appropriate, small amounts of other anti-asthmatics and bronchodilators for example sympathomimetic amines such as isoprenaline, isoetharine, salbutamol, phenylephrine and ephedrine; corticosteroids such as prednisolone and adrenal stimulants such as ACTH may be included.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilised before filling into a suitable vial or ampoule and sealing.

Advantageously, adjuvants such as local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

Compounds of formula (i), or if appropriate a pharmaceutically acceptable salt thereof and/or a pharmaceutically acceptable solvate thereof, may also be administered as a topical formulation in combination with conventional topical excipients.

Topical formulations may be presented as, for instance, ointments, creams or lotions, impregnated dressings, gels, gel sticks, spray and aerosols, and may contain appropriate conventional additives such as preservatives, solvents to assist drug penetration and emollients in ointments and creams. The formulations may contain compatible conventional carriers, such as cream or ointment bases and ethanol or oleyl alcohol for lotions.

Suitable cream, lotion, gel, stick, ointment, spray or aerosol formulations that may be used for compounds of formula (i) or if appropriate a pharmaceutically acceptable salt thereof, are conventional formulations well known in the art, for example, as described in standard text books such as Harry's Cosmeticology published by Leonard Hill Books, Remington's Pharmaceutical Sciences, and the British and US Pharmacopoeias.

Suitably, the compound of formula (i), or if appropriate a pharmaceutically acceptable salt thereof, will comprise from about 0.5 to 20% by weight of the formulation, favourably from about 1 to 10%, for example 2 to 5%.

The dose of the compound used in the treatment of the invention will vary in the usual way with the seriousness of the disorders, the weight of the sufferer, and the relative efficacy of the compound. However, as a general guide suitable unit doses may be 0.1 to 1000 mg, such as 0.5 to 200, 0.5 to 100 or 0.5 to 10mg, for example 0.5, 1, 2, 3, 4 or 5 mg; and such unit doses may be administered more than once a day, for example 2, 3, 4, 5 or 6 times a day, but preferably 1 or 2 times per day, so that the total dry dosage for a 70 kg adult is in the range of about 0.1 to 1000 mg, that is in the range of about 0.001 to 20 mg/kg/day, such as 0.007 to 3, 0.007 to 1.4, 0.007 to 0.14 or 0.01 to 0.5 mg/kg/day, for example 0.01, 0.02, 0.04, 0.05, 0.06, 0.08, 0.1 or 0.2 mg/kg/day, and such therapy may extend for a number of weeks or months.

When used herein the term "pharmaceutically acceptable" encompasses materials suitable for both human and veterinary use.

The following illustrates the invention.

Intermediate 1

2-(METHYLTHIO)PHENYLISOCYANATE

2-Methylmercaptoaniline (69.5 g) was dissolved in ethanol and treated at 0° C. portionwise with concentrated hydrochloric acid (75 ml). The resulting solid was obtained by filtration, washed with isopropanol and dried in vacuo.

This solid was finely ground, suspended in dry dioxane (500 ml) and treated with trichloromethylchloroformate (27 ml) and the mixture refluxed for 18 hours under nitrogen. The solvent was carefully removed in vacuo and the product obtained by distillation. Yield=24.14 g
bp 116–118° C. (15 mm Hg)

Intermediate 2

2-(METHYLTHIO)BENZYLAMINE

A solution of 2-(methylthio)benzonitrile (29.8 g) in dry ether (150 ml) was added dropwise to a stirred suspension of lithium aluminium hydride (1.16 g) in dry ether (360ml) under nitrogen. A thick gum formed which was dissolved by the addition of dry THF (100 ml). The mixture was stirred at room temperature for 2 hours. Water (12 ml) was then carefully added followed by a 15% aqueous solution of sodium hydroxide (36 ml) and more water (12 ml). The mixture was filtered, the filtrate washed with water, dried and evaporated in vacuo. The residue was distilled in vacuo to give a colourless oil. Yield=20.9 g.
bp 139–141° C. (15 mm Hg)

Intermediate 3

1-BENZYL-3-[3-(METHYLTHIO)PHENYL]UREA
Method A 3-(Methylthio)aniline (22.24 g,) was dissolved in dry toluene (300 ml) and to this was added benzyl isocyanate (19.95 g) with stirring. Very soon a thick deposit was formed and stirring was no longer possible. The resulting mixture was allowed to stand overnight at room temperature and hexane (250 ml) then added. The product was filtered off and washed with 1:1 toluene/hexane. Yield=38.89 g.
mp 127–129° C.

Intermediate 4

1-BENZYL-3-(3-CHLOROPHENYL)UREA
Method B

3-Chlorophenylisocyanate (30.7 g) was dissolved in dry toluene (400m1) and benzylamine (23.54 g) added in one portion with stirring. The mixture was stirred for 30 min at room temperature and the product then filtered off and washed with toluene then hexane. Yield=47.53 g.
mp 172–174° C.

Intermediate 5

1-BENZYL-3-(4-CHLOROPHENYL)UREA

Method C

Benzylamine (26.75 g) was dissolved in dry toluene (800 ml) and to this was added 4-chlorophenyl isocyanate (38.38 g) with stirring. After the exotherm had subsided the mixture was heated to boiling and then allowed to stand overnight at room temperature. The product was filtered off and washed with toluene. Yield=64 g.

mp 202–204° C.

Intermediate 6

1-BENZYL-3-[3-(METHOXYCARBONYL) PHENYL]UREA

Method A, mp 148–151° C.

Intermediate 7

1-BENZYL-3-(4-METHOXYPHENYL)UREA

Method B, mp 164–167°

Intermediate 8

1-BENZYL-3-(4-FLUOROPHENYL)UREA

Method B, mp 181–183° C.

Intermediate 9

1-BENZYL-3-(3-FLUOROPHENYL)UREA

Method B, mp 159–160° C.

Intermediate 10

1-BENZYL-3-[(4-(METHYLTHIO)PHENYL] UREA

Method A, mp 173–176° C.

Intermediate 11

1-BENZYL-3-(3-METHOXYPHENYL)UREA

Method A, mp 159–161° C.

Intermediate 12

1-BENZYL-3-(3-BROMOPHENYL)UREA

Method A, mp 173–175° C.

Intermediate 13

1-BENZYL-3-(3-NITROPHENYL)UREA

Method A, mp 193–195° C.

Intermediate 14

1-(THEN-2-YL)-3-(2-METHYLPHENYL)UREA

Method B, mp 188–190° C.

Intermediate 15

1-FURFURYL3-(2-METHYLPHENYL)UREA

Method B, mp 117–119° C.

Intermediate 16

1-(2-FLUOROBENZYL)-3-(4-CHLOROPHENYL) UREA

Method B, mp 195–199° C.

Intermediate 17

1-[2-(TRIFLUOROMETHYL)BENZYL]-3-(2-METHYLPHENYL)UREA

Method A, mp 190–192° C.

Intermediate 16

1-BENZYL-3-(2-METHYLPHENYL)UREA

Method A, mp 189–190° C.

Intermediate 18

1-(2-FLUOROBENZYL)-3-(2-FLUOROPHENYL) UREA

Method B, mp 160–163° C.

Intermediate 19

1-(2-FLUOROBENZYL)-3-[2-(METHYLTHIO) PHENYL]UREA

Method B, mp 135–137° C.

Intermediate 20

1-(2-FLUOROBENZYL)-3-[2-(TRIFLUOROMETHYL)PHENYL]UREA

Method A, mp 178–181° C.

Intermediate 21

1-(2-FLUOROBENZYL)-3-(2-NITROPHENYL) UREA

Method A, mp 169–172° C.

Intermediate 22

1-(2-METHYLPHENYL)-3-[2-(METHYLTHIO) BENZYL]UREA

Method A, mp 214–216° C.

Intermediate 23

1-BENZYL-3-(3-CHLOROPHENYL)-1-(CYANOACETYL)UREA

A mixture of 1-benzyl-3-(3-chlorophenyl)urea (44.78 g) and cyanoacetic acid (16.11 g) was ground together and then acetic anhydride (48 ml) added. The resulting mixture was heated and stirred at 75–80° C. for 16 h. It was then allowed to cool, diluted with ether and the product filtered off and washed with ether. This was then recrystallised from toluene with a hot filtration. Yield=20.15 g.

mp 122–123° C.

The following intermediates were prepared using the above procedure.

Intermediate 24

1-BENZYL-1-(CYANOACETYL)-3-[3-(METHOXYCARBONYL)PHENYL]UREA

The crude material was dissolved in hot toluene and treated with charcoal. The charcoal was removed by filtration and the product recrystallised from toluene.

mp 134–137° C.

Intermediate 25

1-BENZYL-3-(4-CHLOROPHENYL)-1-(CYANOACETYL)UREA mp 100–104° C.

Intermediate 26

1-BENZYL-1-(CYANOACETYL)-3-[3-(METHYLTHIO)PHENYL]UREA mp 113–116° C.

Intermediate 27

1-BENZYL-1-(CYANOACETYL)-3-(4-METHOXYPHENYL)UREA

The crude material was dissolved in hot toluene and treated with charcoal. The charcoal was removed by filtration and the product recrystallised from toluene/hexane.
mp 114–117° C.

Intermediate 28

1-BENZYL-1-CYANOACETYL)-3-(3-FLUOROPHENYL)UREA mp 97–99° C.

Intermediate 29

1-BENZYL-1-(CYANOACETYL)-3-[4-(METHYLTHIO)PHENYL]UREA mp 128–130° C.

Intermediate 30

1-BENZYL-1-(CYANOACETYL)-3-(3-METHOXYPHENYL)UREA

The crude material was dissolved in hot toluene and treated with charcoal. The charcoal was removed by filtration and the product recrystallised from toluene.
mp 127–130° C.

Intermediate 31

1-BENZYL-3-(3-BROMOPHENYL)-1-(CYANOACETYL)UREA

The crude material was dissolved in hot toluene and treated with charcoal. The charcoal was removed by filtration and the product recrystallised from toluene/hexane.
mp 108–121° C.

Intermediate 32

1-(THEN-2-YL)-3-(2-METHYLPHENYL)-1-(CYANOACETYL)UREA mp 127–130° C.

Intermediate 33

1-FURFURYL-3-(2-METHYLPHENYL)-1-(CYANOACETYL)UREA mp 117–119° C.

Intermediate 34

1-(2-FLUOROBENZYL)-3-(4-CHLOROPHENYL)-1-(CYANOACETYL)UREA

This product was washed with ethanol.
mp 125–134° C.

Intermediate 35

6-AMINO-3-BENZYL-1-[3-(METHYLTHIO)PHENYL]URACIL

1-Benzyl-1-(cyanoacetyl)-3-[3-(methylthio)phenyl]urea (14.9 g) was suspended in ethanol (150 ml) and to this was added a solution of sodium hydroxide (2.34 g) in water (30 ml). This was stirred for 1 h then allowed to stand overnight at room temperature. The mixture was filtered to remove a dark impurity and the filtrate carbon treated. This solution was then evaporated to remove ethanol then diluted with water. It was extracted with ethyl acetate (150 ml) and the extracts washed with water (2×75 ml) then dried and evaporated to give a foam. This was taken up in a 1:1 mixture of ethyl acetate and toluene (100 ml). After standing for 1 h the product had precipitated. It was filtered off and washed with 1:1 toluene/hexane (50 ml) then dried to constant weight. Yield=9.06 g.
mp 168–170° C.

Intermediate 36

6-AMINO-3-BENZYL-1-[3-(METHOXYCARBONYL)PHENYL]URACIL

1-Benzyl-1-(cyanoacetyl)-3-[3-(methoxycarbonyl)phenyl]urea (3.51 g) was dissolved in dichloromethane (50 ml) and triethylamine (1.52 g) added. The mixture was stirred for one hour at room temperature and the product filtered off and washed with dichloromethane. Yield=3.16 g.
mp 208–210° C.

The following intermediates were prepared using the above procedure.

Intermediate 37

6-AMINO-3-BENZYL-1-(4-METHOXYPHENYL)URACIL mp 219–221° C.

Intermediate 38

6-AMINO-3-BENZYL-1-(4-CHLOROPHENYL)URACIL mp 246–248° C.

Intermediate 39

6-AMINO-3-(THEN-2-YL)-1-(2-(METHYLPHENYL)URACIL mp 253–256° C.

Intermediate 40

6-AMINO-3-FURFURYL-1-(2-METHYLPHENYL)URACIL mp 241–244° C.

Intermediate 41

6-AMINO-3-(2-FLUOROBENZYL)-1-(4-CHLOROPHENYL)URACIL

The crude material was dissolved in hot ethanol and treated with charcoal. The charcoal was removed by filtration and the product recrystallised from ethanol.
mp 192–212° C.

Intermediate 42

6-AMINO-3-BENZYL-1-(3-FLUOROPHENYL)URACIL mp 228–230° C.

Intermediate 43

6-AMINO-3-BENZYL-1-[4-(METHOXYTHIO)PHENYL]URACIL mp 132–233° C.

Intermediate 44

6AMINO-3-BENZYL-1-(3-METHOXYPHENYL) URACIL

The product was recrystallised from ethanol.
mp 211–214° C.

Intermediate 45

6-AMINO-3-BENZYL-1-(4-FLUOROPHENYL) URACIL

1-Benzyl-1-(cyanoacetyl)-3-(4-fluorophenyl) urea was prepared from the appropriate benzyl urea using the procedure described in the preparation of intermediate 22. The oil produced was used in the above procedure (Intermediate 36) to yield the title compound. Recrystallised from ethyl acetate.
mp 214–2147° C.

The following intermediates were prepared using the above procedure.

Intermediate 46

6-AMINO-1-(2-METHYLPHENYL)-3-[2-(TRIFLUOROMETHYL)BENZYLURACIL

The resulting residue was subjected to column chromatography on silica eluting with ethyl acetate to furnish the title compound.
mp 219–2178° C.

Intermediate 47

6-AMINO-3-BENZYL-1-(2-METHYLPHENYL) URACIL

The crude material was dissolved in hot ethanol and treated with charcoal. The charcoal was removed by filtration and the product recrystallised from ethanol.
mp 194–197° C.

Intermediate 48

6-AMINO-3-(2-FLUOROBENZYL)-1-(2-FLUOROPHENYL)URACIL
mp 207–208° C.

Intermediate 49

6-AMINO-3-(2-FLUOROBENZYL)-1-[2-(METHYLTHIO)PHENYL]URACIL
mp 214–216° C.

Intermediate 50

6-AMINO-3-(2-FLUOROBENZYL)-1-[2-(TRIFLUOROMETHYLPHENYL]URACIL
mp 259–263° C.

Intermediate 51

6-AMINO-3-(2-FLUOROBENZYL)-1-(2-NITROPHENYL)URACIL
mp 250–255° C.

Intermediate 52

6-AMINO-3-BENZYL-1-(3-NITROPHENYL) URACIL

1-Benzyl-3-(3-nitrophenyl)urea (32.53 g) and cyanoacetic acid (11.24 g) were ground together and acetic anhydride (34 ml) was added. The mixture was stirred and heated at 75–80° C. for 30 h. It was then evaporated, taken up in boiling toluene and treated with charcoal. The charcoal was removed by filtration. The resulting solution was allowed to cool and left to stand overnight at room temperature. The resulting solid was filtered off and washed with ether. This solid was dissolved in dichloromethane (100 ml) and triethylamine (3.57 g) added.

The filtrate was also treated with triethylamine (8.55 g). These two solutions were allowed to stand overnight and the precipitated solids were filtered off, washed with dichloromethane and combined to give the title compound (11.32 g).
mp 256–260° C.

Intermediate 53

6-AMINO-1-(2-METHYLPHENYL)-3-[2-(METHYLTHIO)BENZYL]URACIL 1-(2-Methylphenyl)-3-[2-(methylthio)benzyl]urea(23.47 g) and cyanoacetic acid (7.66 g) were ground together and acetic anhydride (23 ml) was added. The mixture was stirred and heated at 75–80° C. for 30 h. Toluene (20 ml) was then added and heating continued for a further 16 hours. The reaction was cooled and filtered. The filtrate was heated to boiling and treated with charcoal. The solid was removed by filtration and the filtrate evaporated in vacuo. The resulting oil was dissolved in dichloromethane (300 ml) and triethylamine (8.15 g) added. The mixture was stirred for 5 hours at room temperature and the solvent removed in vacuo. The residue was purified by column chromatography on silica gel eluting with ethyl acetate and the product was recrystallised from ethyl acetate. Yield=2.60 g.
mp 218–221° C.

EXAMPLE 1

1-BENZYL-3-(3-METHOXYPHENYL) XANTHINE

A mixture of 6-amino-3-benzyl-1-(3-methoxyphenyl) uracil (5.52 g), formic acid (3.2 ml) and sodium nitrite (1.45 g) in formamide (130 ml) was gradually heated up to 100° C. with stirring. Sodium dithionite (4.83 g) was then added in portions over a period of 10 min, the temperature being held at 100° C. The temperature was then raised to 190° C. and the mixture stirred at this temperature for 30 min. It was allowed to cool then extracted into chloroform. The chloroform solution was extracted into 2M sodium hydroxide solution and this washed with ether. The aqueous layer was acidified with concentrated hydrochloric acid to give a solid which was filtered off and washed with water. Recrystallisation from ethanol provided the title compound (1.55 g).
TLC $R_f$ 0.33 (5% methanol/dichloromethane)
mp 205–208° C.

This general procedure was used for all the following xanthines.

EXAMPLE 2

1-BENZYL-3-(3CHLOROPHENYL)XANTHINE

6-Amino-3-benzyl-1-(3-chlorophenyl) uracil was prepared using the procedure described for intermediate 36. The foam produced was used in the procedure of example 1 to yield the title product.
TLC $R_f$ 0.33 (5% methanol/dichloromethane)
mp 245–248° C.

EXAMPLE 3

1-BENZYL-3-(3-FLUOROPHENYL)XANTHINE

Recrystallised from ethanol.
TLC $R_f$ 0.51 (5% methanol/dichloromethane)
mp 203–204° C.

EXAMPLE 4

1-BENZYL-3-[3-(METHYLTHIO)PHENYL] XANTHINE

Recrystallised from ethanol.
TLC $R_f$ 0.44 (5% methanol/dichloromethane)
mp 191–193° C.

EXAMPLE 5

1-BENZYL-3-(4-METHOXYPHENYL) XANTHINE

Recrystallised from ethanol.
TLC $R_f$ 0.30 (5% methanol/dichloromethane)
mp 242–244°

EXAMPLE 6

1-BENZYL-3-(4-FLUOROPHENYL)XANTHINE

Recrystallised from ethanol.
TLC $R_f$ 0.30 (5% methanol/dichloromethane)
mp 252–255° C.

EXAMPLE 7

1-BENZYL-3-[4-(METHYLTHIO)PHENYL] XANTHINE

Recrystallised from ethanol/DMF.
TLC $R_f$ 0.44 (5% methanol/dichloromethane)
mp 260–264° C.

EXAMPLE 8

1-BENZYL-3-3-BROMOPHENYL)XANTHINE

6-Amino-1-(3-bromophenyl)-3-benzyluracil was prepared using the procedure described in the preparation of Intermediate 36. The foam produced was used in the procedure of example 1 to yield the title compound.
Recrystallised from ethanol.
TLC $R_f$ 0.49 (5% methanol/dichloromethane)
mp 253–256° C.

EXAMPLE 9

1-BENZYL-3-(3-NITROPHENYL)XANTHINE

Recrystallised from acetonitrile.
TLC $R_f$ 0.42 (5% methanol/dichloromethane)
mp 227–229° C.

EXAMPLE 10

1-(THEN-2-YL)-3-(2-METHYLPHENYL) XANTHINE

Recrystallised from ethanol.
TLC $R_f$ 0.35 (ethyl acetate)
mp 258–262° C.

EXAMPLE 11

1-(2-FLUOROBENZYL)-3-(4CHLOROPHENYL) XANTHINE

Recrystallised from acetonitrile/DMF.
TLC $R_f$ 0.41 (ethyl acetate)
mp 329–331° C.

EXAMPLE 12

1-BENZYL-3-(2-METHYLPHENYL)XANTHINE

Recrystallised from ethanol.
TLC $R_f$ 0.33 (ethyl acetate)
mp 266–269° C.

EXAMPLE 13

1-(2-FLUOROBENZYL)-3-(2-FLUOROPHENYL) XANTHINE

Recrystallised from ethanol.
TLC $R_f$ 0.35 (ethyl acetate)
mp 253–256° C.

EXAMPLE 14

1-BENZYL-3-(4-CHLOROPHENYL)XANTHINE

Recrystallised from acetonitrile/DMF.
TLC $R_f$ 0.41 (ethyl acetate)
mp 310–313° C.

EXAMPLE 15

1-[2-(TRIFLUOROMETHYL)BENZYL]-3-(2-METHYLPHENYL)XANTHINE

Recrystallised from ethanol.
TLC $R_f$ 0.36 (ethyl acetate)
mp 282–285° C.

EXAMPLE 16

1-(2-FLUOROBENZYL)-3-[2-(METHYLTHIO) PHENYL]XANTHINE

Recrystallised from acetonitrile.
TLC $R_f$ 0.31 (ethyl acetate)
mp 274–279° C.

EXAMPLE 17

1-(2-FLUOROBENZYL)-3-[2-(TRIFLUOROMETHYL)PHENYL]XANTHINE

Recrystallised from ethanol.
TLC $R_f$ 0.31 (ethyl acetate)
mp 273–277° C.

EXAMPLE 18

1-(2-FLUOROBENZYL)-3-(2-NITRO PHENYL) XANTHINE

TLC $R_f$ 0.31 (ethyl acetate)
mp 210–255° C.

EXAMPLE 19

1-(2-FLUOROBENZYL)-3-[2-(TRIFLUOROMETHYL)PHENYL]XANTHINE

Recrystallised from ethanol.
TLC $R_f$ 0.34 (ethyl acetate)
mp 220–233° C.

The following two compounds were prepared using the general procedure with a modified work up as follows:

EXAMPLE 20

1-BENZYL-3-[3-(METHOXYCARBONYL) PHENYL]XANTHINE

On cooling, the reaction mixture was extracted with chloroform. The extracts were washed with water, dried then evaporated. The resulting residue was subjected to column chromatography on silica eluting with ethyl acetate to yield the titled compound.
TLC $R_f$ 0.33 (5% methanol/dichloromethane)
mp 230–232° C.

EXAMPLE 21

1-FURFURYL-3-(2-METHYLPHENYL)XANTHINE

Recrystallised from ethanol.
TLC $R_f$ 0.35 (ethyl acetate)
mp 257–260° C.

EXAMPLE 22

3-(3-AMINOPHENYL)-1-BENZYLXANTHINE

1-Benzyl-3-(3-nitrophenyl)xanthine (1 g) was added to a solution of stannous chloride dihydrate (2.51 g) in concentrated hydrochloric acid (5 ml) and the mixture heated to 60–70° C. with stirring and held at this temperature for 20 min. The reaction mixture was allowed to cool and 40% sodium hydroxide (11 ml) added. The mixture was cooled and the solid filtered off and washed with water (10 ml). It was taken up in 2M sodium hydroxide (10 ml), treated with charcoal, filtered, and the filtrate acidified with glacial acetic acid. The product was filtered off and washed with water. Yield 0.44 g.
TLC $R_f$ 0.24 (5% methanol/dichloromethane)
mp 320–323° C.

EXAMPLE 23

3-(2-AMINOPHENYL)-1-(2-FLUOROBENZYL)XANTHINE

The title compound was prepared using the above procedure.
Recrystallised from acetonitrile.
TLC $R_f$ 0.23 (ethyl acetate)
mp 316–319° C. (d)

EXAMPLE 24

3-(3-ACETAMIDOPHENYL)-1-BENZYLXANTHINE 3-(3-Aminophenyl)-1-benzyl xanthine (0.68 g) was suspended in glacial acetic acid (30 ml). To this was added acetic anhydride (0.25 g) and the mixture was stirred at reflux for 1 h. Water (30 ml) was then added and the product filtered off then washed with water (30 ml). Yield 0.55 g.
TLC $R_f$ 0.19 (5% methanol/dichloromethane)
mp>300° C.

EXAMPLE 25

1-(2-FLUOROBENZYL)-3-[2-(METHYLSULPHONYL)PHENYL]XANTHINE

A solution of 1-(2-fluorobenzyl)-3-[2-(methylthio)phenyl]xanthine (2.8 g) in chloroform (600 ml) and methanol (15 ml) was stirred and maintained below 10° C. during the addition of 3-chloroperbenzoic acid (3.45 g of 80% material). The mixture was stirred for 4 hours at room temperature and then more 3-chloroperbenzoic acid (0.7 g of 80% material) added. The reaction was stirred overnight and then treated with sodium bicarbonate (2.1 g) in water (100 ml). The mixture was stirred for one hour, filtered and the filtrate evaporated in vacuo. The residue was slurried with water, filtered and the solid washed with water. Recrystallised from ethanol/DMF. Yield=1.44 g
TLC $R_f$ 0.19 (ethyl acetate)
mp 264–270° C.

EXAMPLE 26

1-(2-FLUOROBENZYL)-3-[2-(METHYLSULPHONYL)PHENYL]XANTHINE

A solution of 1-(2-fluorobenzyl)-3-[2-(methylthio)phenyl]xanthine (1.15 g) in chloroform (200 ml) and methanol (5 ml) was stirred and maintained at 0–2° C. during the addition of 3-chloroperbenzoic acid (0.65 g of 80% material). The mixture was stirred for 4 hours at 0° C. and then more 3-chloroperbenzoic acid (0.06 g of 80% material) added. The reaction was stirred for one hour at 0° C. and then overnight at room temperature. The mixture was treated with calcium hydroxide (0.3 g). The mixture was stirred for one hour, filtered and the filtrate evaporated in vacuo. The residue was dissolved in dichloromethane, washed with saturated aqueous sodium bicarbonate and then extracted into 1M aqueous sodium hydroxide solution (2×100 ml). The extracts were washed with dichloromethane and the aqueous layer acidified with concentrated hydrochloric acid to give an oil. The oil was extracted with dichloromethane, dried, filtered and the filtrate evaporated to give a solid. The solid was triturated with ether and obtained by filtration. Yield=0.53 g
TLC $R_f$ 0.05 (ethyl acetate)
mp 230–233° C. (dec.)

EXAMPLE 27

1-(2-FLUOROBENZYL)-3-(2-METHYLPHENYL)XANTHINE ortho-Tolylisocyanate (4.95 ml) was added to a solution of 2-fluorobenzylamine (4.56 ml) in toluene (50 ml) under an atmosphere of nitrogen at 5° C. to produce rapid formation of a white solid. Heptane was added, the solid broken up and filtered off to afford 1-(2-fluorobenzyl)-3-(2-methylphenyl)urea (9.5 g) as a white solid. The urea (8 g) and cyanoacetic acid (2.9 g) were ground together and heated in acetic anhydride (15 ml) to 80° C. After cooling the reaction mixture to room temperature, diethyl ether was added and washed with water. The separated ether phase was dried over magnesium sulphate, filtered and evaporated in vacuo to give a crude solid residue (8.9 g). This residue was redissolved in dichloromethane (120 ml), triethylamine (5.7 ml) added and the mixture stirred at room temperature for 3 days. Filtration of the precipitate yielded the desired uracil as a white solid (2.6 g).

The title compound was prepared from this uracil following the general procedure with a modified work up. After the reaction mixture was allowed to cool to room temperature it was extracted into dichloromethane. Attempted extraction into aqueous sodium bicarbonate solution failed to provide any product. However the product precipitated out of the dichloromethane solution and was collected by filtration to afford a white solid (273 mg).
mp 276–277° C.
TLC $R_f$ 0.11 (50% ethyl acetate in hexane)

Assay Methods

The methods used to confirm the phosphodiesterase IV inhibitory activity of compounds of formula (i) are standard assay procedures as disclosed by Schilling et al *Anal. Biochem.* 216 154 (1994), Thompson and Strada *Adv. Cycl. Nucl. Res.* 8 119 (1979) and Gristwood and Owen *Br. J. Pharmacol.* 87 91P (1986).

Compounds of formula (i) have exhibited activity at levels consistent with those believed to be useful in treating phosphodiesterase IV related disease states in those assays.

What is claimed is:

1. A compound of the formula (i):

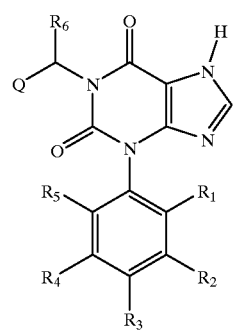

(i)

in which Q represents (a) a 5- to 10-membered aromatic monocyclic or multicyclic hydrocarbon ring in which one or more of the atoms in the ring is an element other than carbon, and is chosen from nitrogen, oxygen or sulphur or (b) a 5- to 10-membered saturated or partially saturated monocyclic or multicyclic hydrocarbon ring in which one or more of the atoms in the ring is an element other than carbon, and is chosen from nitrogen, oxygen or sulphur; either of which is optionally substituted with one or more substituents selected from the group consisting of $C_{1-6}$ alkyl (optionally substituted with one or more halogens), $C_{1-6}$ alkyl—S(O)n— (where n is 0, 1 or 2), —$CO_2H$ (or $C_{1-6}$ alkyl esters thereof or $C_{1-6}$ alkyl amides thereof), halogen, $C_{1-6}$ alkoxy, CN, $NO_2$ and $NR_7R_8$;

$R_1$–$R_5$, which may be the same or different, each represent $C_{1-6}$ alkyl (optionally substituted with one or more halogens), $C_{1-6}$ alkyl—S(O)n— (where n is 0, 1 or 2), —$CO_2H$ (or $C_{1-6}$ alkyl esters thereof or $C_{1-6}$ alkyl amides thereof), halogen, $C_{1-6}$ alkoxy, CN, $NO_2$, $NR_7R_8$ or H (provided $R_1$–$R_6$ are not all H simultaneously);

$R_6$ represents H, $C_{1-6}$ alkyl, —$CO_2H$ (or $C_{1-6}$ alkyl esters thereof or $C_{1-6}$ alkyl amides thereof), —CN, $C_{1-6}$ alkyl optionally substituted by —$CO_2H$ (or $C_{1-6}$ alkyl esters thereof or $C_{1-6}$ alkyl amides thereof), or $C_{1-6}$ alkoxy; and $R_7$ and $R_8$, which may be the same or different, each represent H, $C_{1-6}$ alkyl, $C_{1-6}$ alkylcarbonyl, $C_{1-6}$ alkoxycarbonyl, arylsulphonyl, heteroarylsulphonyl, heterocyclosulphonyl, arylcarbonyl, heteroarylcarbonyl, heterocyclocarbonyl or $C_{1-6}$ alkylsulphonyl, or $R_7$, $R_8$ and the nitrogen to which they are attached form a 5 or 6 membered heterocyclic ring in which the remaining atoms in the ring are chosen from carbon, nitrogen oxygen and sulphur;

and pharmaceutically-acceptable salts thereof.

2. The compound of claim 1, wherein $R_7$ and $R_8$ are independently selected from H, alkyl, alkylcarbonyl, alkoxycarbonyl, arylsulphonyl, arylcarbonyl and alkylsulphonyl, or $NR_7R_8$ is a ring.

3. The compound of claim 1, wherein Q is heteroaryl, optionally substituted by halogen, alkyl, $CF_3$, $NR_7R_8$, alkylS(O)$_{0-2}$, alkoxy or COOH, or (or $C_{1-6}$ alkyl esters or $C_{1-6}$ alkyl amides thereof).

4. The compound of claim 1, wherein $R_1$–$R_5$ are independently selected from the group consisting of $CF_3$, alkyl, alkylS(O)$_{0-2}$, COOH, (or $C_{1-6}$ alkyl esters or $C_{1-6}$ alkyl amides thereof), halogen, alkoxy, $NO_2$, $NR_7R_8$ and H.

5. A method for treating a disease state in a human or animal capable of being modulated by inhibiting production of phosphodiesterase IV, comprising administering to said human or animal suffering from said disease an effective amount of a compound according to claim 1, wherein the disease state is asthma.

6. The compound of claim 1, wherein $R_6$ is H.

7. The compound of claim 1, in the form of an enantiomer or diastereoisomer.

8. A pharmaceutical composition comprising a compound according to claim 1 as active ingredient, in combination with suitable excipients.

9. The compound of claim 1, wherein $R_7$, $R_8$ and the nitrogen to which they are attached form a 5 to 6 membered heterocyclic ring, wherein said 5 or 6 membered ring is selected from the group consisting of morpholine and piperidine.

* * * * *

UNITED STATES PATENT AND TRADEMARK OFFICE
CERTIFICATE OF CORRECTION

PATENT NO. : 6,124,288
DATED : September 26, 2000
INVENTOR(S) : John Gary Montana It is certified that error appears in the above-indentified patent and that said Letters Patent is hereby corrected as shown below:

Column 24, line 13: "nitrogen oxygen" should read --nitrogen, oxygen--.

Column 24, line 21: "COOH, or (or" should read --COOH (or--.

Column 24, line 41: "5 to 6" should read --5 or 6--.

Signed and Sealed this

Eighth Day of May, 2001

NICHOLAS P. GODICI

*Attest:*

*Attesting Officer*     Acting Director of the United States Patent and Trademark Office